United States Patent [19]

Aratani et al.

[11] 4,029,683

[45] June 14, 1977

[54] COPPER COMPLEX

[75] Inventors: Tadatoshi Aratani; Shuzo Nakamura; Tsuneyuki Nagase; Yukio Yoneyoshi, all of Takatsuki, Japan

[73] Assignee: Sumitomo Chemical Company, Limited, Japan

[22] Filed: Dec. 29, 1975

[21] Appl. No.: 645,541

Related U.S. Application Data

[60] Division of Ser. No. 549,034, Feb. 11, 1975, which is a continuation-in-part of Ser. No. 442,413, Feb. 14, 1974, abandoned.

[30] Foreign Application Priority Data

Feb. 14, 1973 Japan .................. 48-18642
June 20, 1973 Japan .................. 48-69997
June 20, 1973 Japan .................. 48-69998

[52] U.S. Cl. .................. 260/438.1; 260/429 C; 260/468 H
[51] Int. Cl.$^2$ .................. C07F 1/08
[58] Field of Search ......... 260/438.1, 429 C, 438.1, 260/429 C

[56] References Cited

UNITED STATES PATENTS

| | | | |
|---|---|---|---|
| 2,300,998 | 11/1942 | White et al. ................ | 260/429 C X |
| 2,381,952 | 8/1945 | Guvelmann ................ | 260/429 C X |
| 3,357,883 | 12/1967 | Pillon et al. ................ | 260/438.1 X |
| 3,868,401 | 2/1975 | Aratani et al. ................ | 260/468 H |

FOREIGN PATENTS OR APPLICATIONS

| | | |
|---|---|---|
| 787,473 | 8/1972 | Belgium |
| 810,959 | 5/1974 | Belgium |
| 740,014 | 11/1955 | United Kingdom |

OTHER PUBLICATIONS

Houghton et al., J. Chem. Soc. pp. 4214–4220 (1965).

Primary Examiner—Helen M. S. Sneed
Attorney, Agent, or Firm—Wenderoth, Lind & Ponack

[57] ABSTRACT

A copper complex coordinated with a Schiff base is provided herein, which complex is especially advantageous to catalyze the asymmetric synthesis of alkyl chrysanthemates. The specific complex of the present invention is a copper complex coordinated with a chiral Schiff base of the formula:

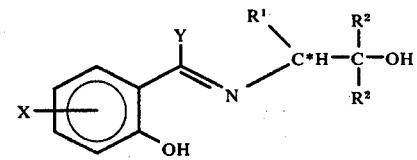

wherein C* is an asymmetric carbon atom, $R^1$ is selected from (a) alkyl groups whose carbon atom number is 1–10, and (b) aralkyl groups with or without alkoxy substituent(s), whose total carbon atom number is 7–20, $R^2$ is selected from aryl groups with alkoxy substituent(s), whose total carbon atom number is 7–30, X is selected from (a) hydrogen, (b) alkyl groups having 1–10 carbon atoms, (c) a phenyl group, (d) alkoxy groups having 1–10 carbon atoms, (e) halogen atoms, (f) nitro, or X is benzo which together with the ring to which it is attached forms a naphthalene ring, and Y is a hydrogen atom.

7 Claims, No Drawings

COPPER COMPLEX

This is a division, of application Ser. No. 549,034, filed Feb. 11, 1975, which is a continuation-in-part of copending application Ser. No. 442,413 filed Feb. 14, 1974, now abandoned.

The present invention is a process for producing an optically active alkyl chrysanthemate wherein 2,5-dimethyl-2,4-hexadiene is reacted with an alkyl diazoacetate in the presence of a copper complex coordinated with a novel kind of Schiff base.

Chrysanthemic acid is an important material for synthetic pyrethroids which are effective as insecticides. There are four stereoisomers of chrysanthemic acid: two kinds of geometric isomers, i.e. cis and trans, each including d and l optical isomers. Among them, the pyrethroids derived from d-trans and d-cis chrysanthemic acids are known to be particularly effective in insecticidal power. In this connection, naturally occurring chrysanthemic acid is known to have d-trans structure.

There can be two industrial methods for obtaining optically active chrysanthemic acid. One is to synthesize a racemic mixture first, which is subsequently subjected to optical resolution, and the other method is direct asymmetric synthesis.

One of the synthetic processes of chrysanthemic acid is to react an alkyl diazoacetate with 2,5-dimethyl-2,4-hexadiene in the presence of a copper catalyst (see Great Britain Pat. No. 740,014) and then to hydrolyze the resulting alkyl chrysanthemate.

This invention relates to the asymmetric synthesis of alkyl chrysanthemates. In our Belgian Pat. No.787,473, there is described and claimed a process for producing an optically active alkyl chrysanthemate by reacting an alkyl diazoacetate with 2,5-dimethyl-2,4-hexadiene in the presence of a copper catalyst coordinated with a chiral ligand according to the following equation:

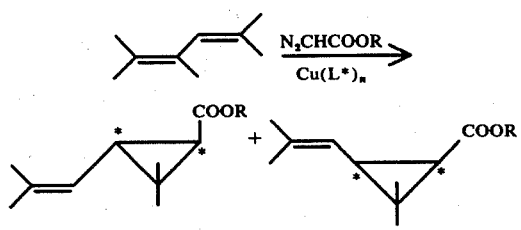

wherein L* is a chiral ligand.

We have now found, according to the present invention, that it is advantageous to catalyze the asymmetric synthesis of alkyl chrysanthemates with novel copper complex coordinated with a novel kind of chiral Schiff base having the following formula:

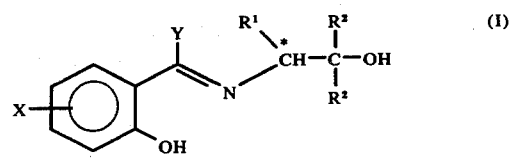

wherein $\overset{*}{C}$ is an asymmetric carbon atom, $R^1$ is selected from the group consisting of (a) alkyl groups whose carbon atom number is 1 - 10, and (b) aralkyl groups with or without alkoxy substituent(s), whose total carbon atom number is 7 - 20, $R^2$ is selected from aryl groups with alkoxy substituent(s), whose total carbon atom number is 7 - 30, X is selected from the group consisting of (a) hydrogen atom, (b) alkyl groups having 1 - 10 carbon atoms, (c) phenyl group, (d) benzo group, (e) alkoxy groups having 1 - 10 carbon atoms, (f) halogen atoms and (g) nitro group, and Y is a hydrogen atom. That is, the present invention relates to a process for producing an optically active alkyl chrysanthemate by reacting 2,5-dimethyl-2,4-hexadiene with an alkyl diazoacetate in the presence of said chiral copper complex.

In the following a further explanation will be given on the chiral copper complexes used as catalysts in the present invention.

When the Schiff base of the formula (I) forms a metal complex with divalent copper ion, two kinds of chelate are possible. (for the chemistry of metal complexes of Schiff bases, see R. H. Holm, G. W. Everett, Jr., and A. Chakravorty "Progress in Inorganic Chemistry" 7, 83-214, (1966), Interscience Publishers, New York).

One has the following dimeric structure (II) wherein the Schiff base behaves as tridentate ligand:

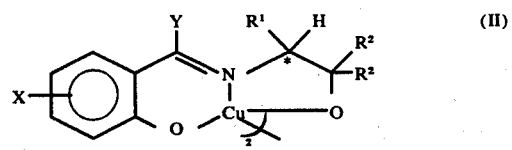

wherein $R^1$, $R^2$, X and Y are as defined above. The other has the following monomeric structure (III) wherein the Schiff base behaves as bidentate ligand:

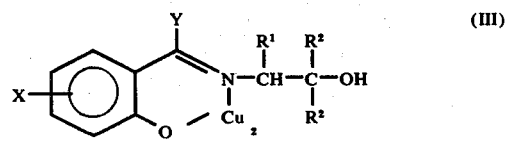

wherein $R^1$, $R^2$, X and Y are as defined above. (for the copper complexes of N-salicylidene-2-aminoethanol, see R. P. Houghton and D. J. Pointer, J. Chem. Soc. 4214 (1965).

The binuclear copper complex of the formula (II) used as catalyst in the present invention is prepared by the reaction of a Schiff base of the formula (I) with a cupric salt such as cupric acetate etc. The mononuclear copper complex of the formula (III) is simply obtained by the reaction of an amino alcohol having the following defined formula (IV) and a bis (salicylaldehydato) copper or a derivative thereof.

The chiral Schiff base of the formula (I) is synthesized by the reaction of a chiral amino alcohol having the formula (IV) with a salicylaldehyde derivative having the formula (V):

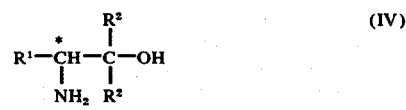

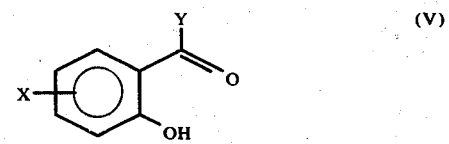

wherein $R^1$, $R^2$, X and Y are as defined above.

Specific examples of the substituents $R^1$ and $R^2$ in the amino alcohol (IV) are methyl, ethyl, propyl, isopropyl, butyl, isobutyl, 2-butyl, -t-butyl, hexyl, octyl, cyclohexyl, cyclohexylmethyl, phenyl, benzyl, benzhydryl, 2,2-diphenylethyl, tolyl, α-naphthyl and β-naphthyl. Among these examples, preferred substituents of $R^1$ are methyl, isopropyl, isobutyl, cyclohexylmethyl, benzyl and a benzyl group having a substituent at the 4-position of the aromatic nucleus, of which the substituent is, for example, methoxy, ethoxy, propoxy, isopropoxy, butoxy, hexyloxy, octyloxy, or benzyloxy, etc. As $R^2$ in the amino alcohol, a phenyl group having a substituent at the 2-position or having substituents at the 2,5-positions is preferred. Specific examples of 2-substituted phenyl groups are 2-methoxyphenyl, 2-ethoxyphenyl, 2-propoxyphenyl, 2-isopropoxyphenyl, 2-butoxyphenyl, 2-t-butoxyphenyl, 2-hexyloxyphenyl, 2-oxtyloxyphenyl, 2-henzyloxyphenyl, 2-phenoxyphenyl, etc. Specific examples of 2,5-substituted phenyl groups are 2-methoxy-5-methylphenyl, 2-butoxy-5-methylphenyl, 5-methyl-2-octyloxyphenyl, 2-benzyloxy-5-methylphenyl, 5-t-butyl-2-methoxyphenyl, 2-butoxy-5-t-butylphenyl, 5-t-butyl-2-octyloxyphenyl, 2-benzoxy-5-t-butylphenyl, 4-methoxybiphenyl-3-yl, 4-butoxybiphenyl-3-yl, 4-octyloxybiphenyl-3-yl, 4-benzyloxybiphenyl-3-yl, 2,5-dimethoxyphenyl, 2,5-dibutoxyphenyl, 2,5-dioctyloxyphenyl, 2,5-dibenzyloxyphenyl, etc.

The optically active amino alcohols of the formula (IV) to be used in this invention may be prepared in any of the following two ways, i.e. one is to optically resolve a racemic mixture of the corresponding alcohol with a proper optical resolution agent, and the other is to derive the same from the corresponding optically active precursor. Thus, for example, when an optically active amino acid ester of the following formula (VI) is reacted with a Grignard reagent of the following formula (VII) there is obtained the optically active amino alcohol (IV):

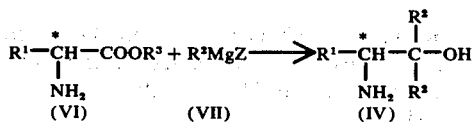

wherein $R^1$, $R^2$ is alkyl, aryl or aralkyl, $R^3$ is alkyl or benzyl of 1 – 10 carbon atos and Z is chlorine, bromine or iodine. As for the addition reaction of phenyl magnesium bromide to (L)-alanine ethyl ester, references may be made for example to A. McKenzie, R. Roger, G. O. Willis, J. Chem. Soc., 779 (1926) and B. M. Benjamin, H. J. Schaefer, C. J. Collins, J. Am. Chem. Soc. 79, 6160 (1957).

Further, the substituent X in the salicylaldehyde derivative (V) employed in the synthesis of the chiral Schiff base is a hydrgen atom, alkyl group, aralkyl group, aryl group, or a substituent containing a heteroatom, and the substituent Y is a hydrogen atom, alkyl group, aralkyl group, or aryl group.

Specific examples of the reactive substituents containing (a) hetero-atom(s) are OH, OR, OCOR, CHO, COR, COOH, COOR, CN, $CONH_2$, $NH_2$, NHR, $NR_2$, NHCOR, $NO_2$, SH, SR, SOR, $SO_2R$, $SO_3H$, $SO_3R$, a halogen atom etc. wherein R is alkyl, aralkyl or aryl.

Specific examples of the salicylaldehyde derivatives (V) are salicylaldehyde, 3-ethoxysalicylaldehyde, O-vanilline, 3,5-dibromosalicylaldehyde, 5-chlorosalicylaldehyde, 3-nitrosalicyladehyde, 3-isopropyl-6-methylsalicylaldehyde, 2-hydroxyl-naphthaldehyde, 1-hydroxy-2-naphthaldehyde and the like.

Among the chiral copper complexes employed as catalysts in the present invention, specific examples of the binuclear copper complexes (II) are those that are derived from the following chiral Schiff bases:

a. N-salicylidene-2-amino-1,1-di(2-isopropoxyphenyl)-3-phenyl-1-propanol,
b. N-salicylidene-2-amino-1,1-di(2-butoxy-5-t-butylphenyl)-3-phenyl-1-propanol,
c. N-salicylidene-2-amino-1,1-di(2-methoxyphenyl)-3-phenyl-1-propanol,
d. N-salicylidene-2-amino-1,1-di(2-ethoxyphenyl)-3-phenyl-1-propanol,
e. N-salicylidene-2-amino-1,1-di(2-butoxyphenyl)-3-phenyl-1-propanol,
f. N-salicylidene-2-amino-1,1-di(2-octyloxyphenyl)-3-phenyl-1-propanol,
g. N-salicylidene-2-amino-1,1-di(2-phenoxyphenyl)-3-phenyl-1-propanol,
h. N-salicylidene-2-amino-1,1-di(2-benzyloxy-5-methylphenyl)-3-phenyl-1-propanol,
i. N-salicylidene-2-amino-1,1-di(5-t-butyl-2-isopropoxyphenyl)-3-phenyl-1-propanol,
j. N-salicylidene-2-amino-1,1-di(5-t-butyl-2-octyloxyphenyl)-3-phenyl-1-propanol,
k. N-salicylidene-2-amino-1,1-di(4-butoxybiphenyl-3-yl)-3-phenyl-1-propanol,
l. N-salicylidene-2-amino-1,1-di(2,5-dibutoxyphenyl)-3-phenyl-1-propanol,
m. N-salicylidene-2-amino-1,1-di(2-isopropoxyphenyl)-3-(4-isopropoxyphenyl)-1-propanol,
n. N-salicylidene-2-amino-1,1-di(5-t-butyl-2-octyloxyphenyl)-3-(4-isopropoxyphenyl)-1-propanol,
o. N-salicylidene-2-amino-1,1-di(2-butoxyphenyl)-3-cyclohexyl-1-propanol,
p. N-salicylidene-2-amino-1,1-di(2-methoxyphenyl)-4-methyl-1-pentanol,
q. N-salicylidene-2-amino-1,1-di(2-butoxy-5-t-butylphenyl)-4-methyl-1-pentanol,
r. N-salicylidene-2-amino-1,1-di(2-benzyloxy-5-t-butylphenyl)-4-methyl-1-pentanol,
s. N-salicylidene-2-amino-1,1-di(2-butoxy-5-t-butylphenyl)-1-propanol,
t. N-salicylidene-2-amino-1,1-di(2-butoxyphenyl)-3-methyl-1-butanol,
u. N-salicylidene-2-amino-1,1-di(2-butoxyphenyl)-1-propanol,
v. N-(3,5-dibromosalicylidene)-2-amino-1,1-di(2-isopropoxyphenyl)-3-phenyl-1-propanol,
w. N-(3-ethoxysalicylidene)-2-amino-1,1-di(2-isopropoxyphenyl)-3-phenyl-1-propanol,
x. N-(2-hydroxyl-1naphthylmethylene)-2-amino-1,1-di(2-isopropoxyphenyl)-3-phenyl-1-propanol, or
y. N-salicylidene-2-amino-1,1-di(4-butoxybiphenyl-3-yl)-1-propanol.

Specific examples of the mononuclear copper complexes (III) are those that are derived from the following chiral Schiff bases:

a. N-salicylidene-2-amino-1,1-di(2-methoxyphenyl)-3-phenyl-1-propanol,
b. N-salicylidene-2-amino-1,1-di(3-methoxyphenyl)-3-phenyl-1-propanol, or
c. N-salicylidene-2-amino-1,1-di(2-methoxyphenyl)-4-methyl-1-pentanol.

In the actual practice of the present invention, the reaction can be carried out regardless of whether the chiral copper complex employed as catalyst is soluble or insoluble in the reaction system.

The catalyst may be recovered and purified by appropriate method for repeated uses.

Preferably, the molar ratio of the copper complex to alkyl diazoacetate is in a range of 0.001 – 0.1.

There is no particular restriction on the choice of the alcoholic part of the alkyl diazoacetate used in the reaction of the present invention, though normally lower aliphatic alcohols having 1 to 8 carbon atoms are employed.

The reaction of the present invention can be carried out either in the absence or presence of a solvent.

Although the reaction temperature is not particularly limited, usually a temperature between −50° C. and 150° C. is suitable. In particular cases of carrying out the reaction at a temperature below the melting point of 2,5-dimethyl-2,4-hexadiene (15° C.), a suitable solvent may be desirably added to the reaction system. Aromatic hydrocarbons such as bensene, toluene and xylene are suitable solvents in such cases.

The present invention is explained in further detail by the example set forth below. They are not, however, to be taken as being limitative thereof.

In general unequivocal coorelation exists between the absolute configuration of the substance which induces the asymmetry and that of the substance to which the asymmetry is induced. Therefore, in this invention, too, it is needless to say that when the enatiomeric copper complex of the one described in the following examples is used as the catalyst, the resulting alkyl chrysanthemate and chrysanthemic acid will also have the enantiomeric structure.

EXAMPLE 1

An amount of 0.47 g. (0.4 millimol) of the binuclear copper complex of (R)-N-salicylidene-2-amino-1,1-di(2-isopropoxyphenyl)-3-phenyl-1-propanol (corresponding to the formula (II) wherein $R^1$ = benzyl, $R^2$ = 2-isopropoxyphenyl, and X = Y = hydrogen) was dissolved in 8.8 g. (80 millimols) of 2,5-dimethyl-2,4-hexadiene. To this solution, a mixture of 8.8 g. (80 millimols) of the above-mentioned diene and 4.6 g. (40 millimols) of ethyl diazoacetate was added dropwise under stirring over a period of 6 hours. At the beginning of the addition, the reaction system was one heated to 70° C. to facilitate the decomposition of diazoacetate and thereafter the temperature was maintained at 40° C. At the end of the addition, evolution of a nearly quantitative amount of nitrogen gas was observed.

From the reaction mixture, unreacted excess diene (boiling point: 40° C./20 mmHg) was distilled off under reduced pressure, and 4.1 g. of ethyl chrysanthemate was obtained as an oil having a boiling point of 60° C./0.5 mmHg, the yield being 53% with respect to the diazo compound.

This sample represented an optical rotation $\alpha_D$ of +8.80° (neat, 1 dm) and the ratio of cis/trans isomer of the ethyl chrysanthemate was 42/58 (as determined by gas chromatography).

Chrysanthemic acid was obtained by the hydrolysis of this ester. The acid, after distillation, represented specific optical rotation $[\alpha]_D$ of +25.48° (c 5.07, chloroform). Gas chromatographic analysis showed that the composition of the four optical isomers of this sample was as follows:

d-trans isomer: 43.0%,
d-cis isomer: 30.3%,
l-trans isomer: 16.1%,
l-cis isomer: 10.6%.

(for the analytical method, see A. Murano, Agr. Biol. Chem., 36, 2203 (1972)

EXAMPLE 2

A similar reaction to Example 1 was carried out using 0.58 g. of the copper complex of (R)-N-salicylidene-2-amino-1,1-di(2-butoxy-5-t-butylphenyl)-3-phenyl-1-propanol (corresponding to the formula (II) wherein $R^1$ = benzyl, $R^2$ = 2-butoxy-5-t-butylphenyl, and X = Y = hydrogen) to give 4.0 g. of ethyl chrysanthemate. Reaction temperature, 40° C.; chemical yield, 52%; cis/trans ratio, 43/57; and optical rotation, $\alpha_D$ +10.26 (neat, 1 dm). The chrysanthemic acid was obtained by the hydrolysis of this ester to show specific optical rotation $[\alpha]_D$ of +29.84° (c 5.12, chloroform). The composition of the optical isomers was as follows:

d-trans isomer: 44.7%,
d-cis isomer: 33.8%,
l-trans isomer: 10.6%,
l-cis isomer: 10.9%.

EXAMPLES 3 to 41

In a similar manner to Example 1, optically active ethyl chrysanthemate and chrysanthemic acid were synthesized, using other kinds of chiral binuclear copper complexes of the formula (II). The results are summarized in Table 1.

Table 1

| | | Asymetric synthesis with binuclear copper complexes | | | | | | |
|---|---|---|---|---|---|---|---|---|
| | | | | | | Ethyl Chrysanthemate | | Chrysanthemic acid |
| Example | Chiral Schiff base | Copper complex (g.) | Toluene (ml.) | Temp. (° C.) | Chem. yield (%) | cis/trans | $\alpha_D$ (neat) (1 dm) | $[\alpha]_D$ (Chloroform) |
| 3 | (S)-N-salicylidene-2-amino-1,1-di(2-methoxyphenyl)-3-phenyl-1-propanol | 0.42 | 0 | 40 | 58 | 38/62 | −8.01 | −23.10 |
| 4 | (S)-N-salicylidene-2-amino-1,1-di(2-ethoxyphenyl)-3-phenyl-1-propanol | 0.45 | 0 | 50 | 58 | 38/62 | −8.65 | −21.70 |
| 5 | (S)-N-salicylidene-2-amino-1,1-di(2-butoxyphenyl)-3-phenyl-1-propanol | 0.50 | 0 | 50 | 69 | 39/61 | −8.80 | −24.50 |
| 6 | (R)-N-salicylidene-2-amino-1,1-di(2- | 0.58 | 0 | 40 | 65 | 38/62 | +9.03 | +26.86 |

Table 1-continued

Asymmetric synthesis with binuclear copper complexes

| Example | Chiral Schiff base | Copper complex (g.) | Toluene (ml.) | Temp. (° C.) | Ethyl Chrysanthemate Chem. yield (%) | cis/trans | $\alpha_D$ (neat) (1 dm) | Chrysanthemic acid $[\alpha]_D$ (Chloroform) |
|---|---|---|---|---|---|---|---|---|
| 7 | (R)-N-salicylidene-2-amino-1,1-di(2-phenoxyphenyl)-3-phenyl-1-propanol octyloxyphenyl)-3-phenyl-1-propanol | 0.56 | 0 | 40 | 56 | 33/67 | +5.28 | — |
| 8 | (S)-N-salicylidene-2-amino-1,1-di(2-benzyloxy-5-methylphenyl)-3-phenyl-1-propanol | 0.57 | 10 | 40 | 61 | 42/58 | −8.93 | — |
| 9 | (S)-N-salicylidene-2-amino-1,1-di(5-t-butyl-2-isopropoxy-phenyl)-3-phenyl-1-propanol | 0.56 | 0 | 40 | 59 | 39/61 | −10.88 | −30.06 |
| 10 | (R)-N-salicylidene-2-amino-1,1-di(5-t-butyl-2-octyloxyphenyl-3-phenyl-1-propanol | 0.67 | 0 | 40 | 60 | 43/57 | +10.17 | +30.29 |
| 11 | (R)-N-salicylidene-2-amino-1,1-di(4-butoxybiphenyl-3-yl)-3-phenyl-1-propanol | 0.61 | 0 | 40 | 59 | 40/60 | +8.64 | — |
| 12 | (R)-N-salicylidene-2-amino-1,1-di(2,5-dibutoxyphenyl)-3-phenyl-1-propanol | 0.59 | 0 | 40 | 63 | 38/62 | +10.65 | — |
| 13 | (S)-N-salicylidene-2-amino-1,1-di(2-isopropoxyphenyl)-3-(4-isopropoxyphenyl)-1-propanol | 0.52 | 0 | 40 | 55 | 39/51 | −10.81 | — |
| 14 | (S)-N-salicylidene-2-amino-1,1-di(5-t-butyl-2-octyloxyphenyl)-3-(4-isopropoxyphenyl)-1-propanol | 0.72 | 0 | 40 | 51 | 41/59 | −11.41 | −34.65 |
| 15 | (S)-N-salicylidene-2-amino-1,1-di(2-butoxyphenyl)-3-cyclohexyl-1-propanol | 0.50 | 0 | 40 | 53 | 35/65 | −8.89 | — |
| 16 | (S)-N-salicylidene-2-amino-1,1-di(2-methoxyphenyl)-4-methyl-1-pentanol | 0.40 | 0 | 40 | 54 | 41/59 | −5.78 | — |
| 17 | (S)-N-salicylidene-2-amino-1,1-di(2-butoxy-5-t-butyl-phenyl)-4-methyl-1-pentanol | 0.64 | 0 | 40 | 47 | 42/58 | −5.65 | — |
| 18 | (S)-N-salicylidene-2-amino-1,1-di(2-benzyloxy-5-t-butylphenyl)-4-methyl-1-pentanol | 0.62 | 0 | 40 | 46 | 43/57 | −5.35 | — |
| 19 | (S)-N-salicylidene-2-amino-1,1-di(2-butoxy-5-t-butyl-phenyl)-1-propanol | 0.55 | 0 | 40 | 54 | 42/58 | −11.58 | −35.84 |
| 20 | (S)-N-salicylidene-2-amino-1,1-di(2-butoxyphenyl)-3-methyl-1-butanol | 0.44 | 0 | 40 | 52 | 42/58 | −6.11 | — |
| 21 | (S)-N-salicylidene-2-amino-1,1-di(2-butoxyphenyl)-1-propanol | 0.41 | 0 | 40 | 63 | 41/59 | −9.20 | — |
| 22 | (R)-N-(3,5-dibromo-salicylidene)-2-amino-1,1-di(2-isopropoxyphenyl)-3-phenyl-1-propanol | 1.09 | 0 | 30 | 71 | 40/60 | +8.77 | — |
| 23 | (R)-N-(3-ethoxysalicylidene)-2-amino-1,1-di(2-isopropoxyphenyl)-3-phenyl-1-propanol | 0.91 | 0 | 30 | 57 | 42/58 | +7.02 | — |
| 24 | (R)-N-(2-hydroxy-1-naphthylmethylene)-2-amino-1,1-di(2-isopropoxyphenyl)-3-phenyl-1-propanol | 0.92 | 0 | 30 | 63 | 41/59 | +9.55 | +25.84 |
| 25 | N-salicylidene(S)-2-amino-1,1-di(2-3'-oxapentoxy-5-t-butyl- | 0.53 | 0 | 40 | 60 | — | −10.60 | — |

Table 1-continued

Asymetric synthesis with binuclear copper complexes

| Example | Chiral Schiff base | Copper complex (g.) | Toluene (ml.) | Temp. (°C.) | Ethyl Chrysanthemate Chem. yield (%) | cis/trans | $\alpha_D$ (neat) (1 dm) | Chrysanthemic acid $[\alpha]_D$ (Chloroform) |
|---|---|---|---|---|---|---|---|---|
| 26 | phenyl)-1-propanol N-salicylidene(S)-2-amino-1,1-di(2-cyclohexyloxy-5-t-butylphenyl)-1-propanol | 0.56 | 0 | 40 | 58 | — | −9.63 | — |
| 27 | (N-salicylidene(R)-2-amino-1,1-di(2-cyclohexyloxy-5-t-butylpenyl)-3-phenyl-1-propanol | 0.60 | 0 | 40 | 60 | — | +9.92 | — |
| 28 | N-salicylidene(S)-2-amino-1,1-di(2-t-butoxy-5-t-butyl-phenyl)-1-propanol | 1.05 | 0 | 40 | 60 | 42/58 | −8.88 | — |
| 29 | N-Salicylidene(S)-2-amino-1,1-di(2-iso-propoxy-5-methyl-phenyl)-1-propanol | 0.86 | 0 | 40 | 46 | 41/59 | −7.16 | — |
| 30 | N-salicylidene(S)-2-amino-1,1-di(2-benzyloxy-4-t-butylphenyl)-1-propanol | 0.56 | 0 | 40 | 58 | 43/57 | −5.70 | −16.79 |
| 31 | N-salicylidene(S)-2-amino-1,1-di(2-sec-butoxy-5-t-butylphenyl)-1-propanol | 0.60 | 0 | 40 | 51 | 41/59 | −7.40 | −21.24 |
| 32 | N-salicylidene(S)-2-amino-1,1-di(2-benzyloxy-5-t-butylphenyl)-1-propanol | 0.56 | 0 | 40 | 57 | 42/58 | −7.27 | — |
| 33 | N-salicylidene(S)-2-amino-1,1-di(2-butoxy-4-t-butylphenyl)-1-propanol | 0.52 | 0 | 40 | 56 | 48/52 | −8.20 | — |
| 34 | N-salicylidene(S)-2-amino-1,1-di(2,5-dibutoxyphenyl)-1-propanol | 0.53 | 0 | 40 | 63 | 40/60 | −6.72 | — |
| 35 | N-salicylidene(S)-2-amino-1,1-di(4-octyloxy-3-biphenyl)-1-propanol | 0.50 | 0 | 40 | 59 | 38/62 | −5.35 | — |
| 36 | N-salicylidene(S)-2-amino-1,1-di(4-butoxy-3-biphenyl)-1-propanol | 0.56 | 0 | 40 | 66 | 42/58 | −11.28 | −31.69 |
| 37 | N-salicylidene(S)-2-amino-1,1-di(5-t-butyl-2-ocyloxy-phenyl)-1-propanol | 0.60 | 0 | 40 | 54 | 49/51 | −13.52 | −38.76 |
| 38 | N-salicylidene(S)-2-amino-1,1-di(2-butoxy-5-methylphenyl)-1-propanol | 0.45 | 0 | 40 | 60 | 41/59 | −7.22 | −20.46 |
| 39 | N-salicylidene(S)-2-amino-1,1-di(2-butoxy-5-t-butyl-phenyl)-3-(4-benzyl-oxyphenyl)-1-propanol | 0.66 | 0 | 40 | 57 | — | −9.70 | −29.92 |
| 40 | N-salicylidene(S)-2-amino-1,1-di(2-butoxy-5-t-butyl-phenyl)-3-methyl-1-butanol | 0.55 | 0 | 40 | 59 | — | −9.67 | −24.60 |
| 41 | N-salicylidene(S)-2-amino-1,1-di(2-butoxyphenyl)-4-methyl-1-pentanol | 0.46 | 0 | 40 | 58 | — | −5.88 | −17.31 |

EXAMPLE 42

An amount of 1.20 g. (1.2 millimols) of the mononuclear copper complex of (R)-N-salicylidene-2-amino-1,1-di(2-methoxyphenyl)-3-phenyl-1-propanol (corresponding to the formula (III) wherein $R^1$ = benzyl, $R^2$ = methoxyphenyl, and X = Y = hydrogen) was dissoled in a mixture of 60 ml. toluene and 13.2 g. (120 millimols) 2,5-dimethyl-2,4-hexadiene. To this solution, a mixture of 13.2 g. (120 millimols) of the above-mentioned diene and 4.6 g. (40 millimols) of ethyl diazoacetate was added dropwise under stirring over a period of 11 hours. At the beginning of the addition, the reaction system was once heated to 85° C. and thereafter the temperature was maintained at 0° C. At the end of the addition, nearly quantitative amount of nitrogen gas was evolved.

On distilling off unreacted excess diene under reduced pressure, 3.7 g. of ethyl chrysanthemate (yield: 47% with respect to the diazo compound) was obtained. This ester represented an optical rotation $\alpha_D$ of +10.4° (neat, 1 dm), and the ratio of cis/trans isomer was 38/62 (as determined by gas chromatography).

The chrysanthemic acid was obtained by the hydrolysis of the ester to show a specific optical rotation $[\alpha]_D$ of +27.78° (c 5.49, chloroform). This product was analyzed for the four optical isomers by gas chromatography. The results were as follows:

d-trans isomer: 46.7%,
d-cis isomer: 29.4%,
l-trans isomer: 14.6%,
l-cis isomer: 9.3%.

EXAMPLES 43 and 44

In a similar manner to Example 25, optically active ethyl chrysanthemate and chrysanthemic acid were synthesized, using other two kinds of mononuclear copper complexes of the formula (III). The results are summarized in Table 2.

tion mixture, the residue was dissolved in 35 ml. benzene and the solution was washed with a 50 ml. saturated aqueous solution of sodium bicarbonate. The organic layer was washed with water and dried. After evaporation of the solvent the resulting precipitate was collected by filtration and washed twice with 10 ml. methanol. Upon drying the solids under reduced pressure, binuclear copper complex of (R)-N-salicylidene-2-amino-1,1-di(2-isopropoxyphenyl)-1-propanol was obtained as grayish blue crystals. Yield, 1.93 g. (86%), $[\alpha]_{546}$, +1360° (c 0.143, benzene), melting point, 178° – 179° C. (decomposed).

| Elemental analysis for $C_{68}H_{70}Cu_2N_2O_8$ | | | | |
|---|---|---|---|---|
| | C (%) | H (%) | N (%) | Cu (%) |
| Found: | 69.41 | 6.06 | 2.98 | 11.00 |
| Calculated: | 69.78 | 6.03 | 2.39 | 10.86 |

Magnetic susceptibility $\mu = 0.86$ B.M.

0.5 g. of the above-mentioned copper complex was dissolved in 10 ml. pyridine. Upon adding 50 ml. water to this solution, bluish white solids separated out. When the solids were washed with 10 ml. methanol, a mononuclear copper complex containing one mol of pyridine

Table 2

| | | Asymmetric synthesis with mononuclear copper complexes | | | | | | |
|---|---|---|---|---|---|---|---|---|
| | | | | | | Ethyl Chrysanthemate | | Chrysanthemic acid |
| Example | Chiral Schiff base | Copper complex (g.) | Toluene (ml.) | Temp. (° C.) | Chem. Yield (%) | cis/trans | $\alpha_D$ (neat) (1 dm) | $[\alpha]_D$ (Chloroform) |
| 43 | (R)-N-salicylidene-2-amino-1,1-di(3-methoxyphenyl)-3-phenyl-1-propanol | 0.42 | 0 | 40 | 57 | 34/66 | +3.31 | — |
| 44 | (S)-N-salicylidene-2-amino-1,1-di(2-methoxyphenyl)-4-methyl-1-pentanol | 0.37 | 0 | 40 | 59 | 36/64 | −9.54 | — |

EXAMPLE 1A

A mixture of 2.5 g. (5.9 millimols) of (R)-2-amino-1,1-di(2-isopropoxyphenyl)-3-phenyl-1-propanol {$[\alpha]_D$ +65.0° (c 1.0, chloroform)} and 0.66 g. (5.4 millimols of salicylaldehyde in 50 ml benzene was heated under reflux for 2.5 hours. After the distillation of the solvent from the reaction mixture, the residue was recrystallized from ethanol to give (R)-N-salicylidene-2-amino-1,1-di(2-isopropoxyphenyl)-3-phenyl-1-propanol as yellow crystals. Yield, 2.43 g. (85%); melting point, 152°– 153° C.; $[\alpha]_D$, +65.25° (c 1.00, chloroform).

| Elemental analysis for $C_{34}H_{37}NO_4$ | | | |
|---|---|---|---|
| | C (%) | H (%) | N (%) |
| Found: | 77.81 | 7.26 | 2.62 |
| Calculated: | 77.98 | 7.12 | 2.68 |

EXAMPLE 1B

Two grams (3.82 millimols) of the Schiff base obtained in Example 1A and 0.78 g. (3.9 millimols) of cupric acetate monohydrate were dissolved in 20 ml. ethanol, and the solution was heated under reflux for 10 minutes. After removal of the solvent from the reaction mixture, the residue was dissolved in 35 ml. benwas obtained as red crystals. Yield, 0.50 g. (88%), $[\alpha]_{546}$, +2320° (c 0.876, benzene), melting point, 186° – 188° C. (decomposed).

| Elemental analysis for $C_{34}H_{35}CuNO_4 \cdot C_5H_5N$ | | | | |
|---|---|---|---|---|
| | C (%) | H (%) | N (%) | Cu (%) |
| Found: | 70.65 | 6.31 | 4.20 | 9.77 |
| Calculated: | 70.51 | 6.07 | 4.22 | 9.57 |

Magnetic susceptibility $\mu = 1.87$ B.M.

EXAMPLES 2A to 41A

In a similar manner to Example 1A, other 40 kinds of chiral Schiff bases of the formula (I) were synthesized from chiral amino alcohols of the formula (IV) and salicylaldehyde derivatives of the formula (V). The results are summarized in Table 3.

EXAMPLES 2B to 41B

In a similar manner to Example 1B, other 40 kinds of chiral binuclear copper complexes of the formula (II) were synthesized from the chiral Schiff bases of the formula (I) and cupric acetate. The results are summarized in Table 3.

Table 3

Chiral Schiff bases and binuclear copper complexes

| Example | Compound | Yield (%) | m.p. (°C.) | Specific* rotation (deg.) | C (%) | H (%) | N (%) | Cu (%) |
|---|---|---|---|---|---|---|---|---|
| 2A | (R)-N-salicylidene-2-amino-1,1-di(2-butoxy-5-t-butylphenyl)-3-phenyl-1-propanol | 90 | oil | — | — | — | — | — |
| 2B | Copper complex of the above Schiff base | 72 | — | +1040 (benzene) | 72.91 (72.85 | 7.71 7.64 | 1.98 1.93 | 8.56 8.76) |
| 3A | (S)-N-salicylidene-2-amino-1,1-di(2-methoxyphenyl)-3-phenyl-1-propanol | 70 | 80.9 | −65.2 (chloroform) | 76.83 (77.06 | 6.23 6.25 | 2.81 3.00) | — |
| 3B | Copper complex of the above Schiff base | 70 | 150 (dec.) | −1500 (toluene) | 68.73 (68.10 | 5.35 5.14 | 2.61 2.65 | 11.98 12.01) |
| 4A | (S)-N-salicylidene-2-amino-1,1-di(2-ethoxyphenyl)-3-phenyl-1-propanol | 85 | oil | — | — | — | — | — |
| 4B | Copper complex of the above Schiff base | 79 | — | −1240 (ethanol) | 69.13 (68.99 | 5.44 5.61 | 2.72 2.51 | 11.50 11.41) |
| 5A | (S)-N-salicylidene-2-amino-1,1-di(2-butoxyphenyl)-3-phenyl-1-propanol | 85 | 119–121 | −60.3 (chloroform) | 78.42 (78.37 | 7.53 7.49 | 2.60 2.54) | — |
| 5B | Copper complex of the above Schiff base | 92 | — | −1170 (ethanol) | 70.19 (70.50 | 6.50 6.41 | 2.21 2.28 | 11.35 10.36) |
| 6A | (R)-N-salicylidene-2-amino-1,1-di(2-octyloxyphenyl)-3-phenyl-1-propanol | 67 | — | +52.8 (chloroform) | 80.73 (79.60 | 9.17 8.65 | 2.06 2.11) | — |
| 6B | Copper complex of the above Schiff base | 88 | — | +1140 (benzene) | 72.61 (72.85 | 7.82 7.64 | 1.69 1.93 | 6.99 8.76) |
| 7A | (R)-N-salicylidene-2-amino-1,1-di(2-phenoxyphenyl)-3-phenyl-1-propanol | 93 | 150.4 | +57.9 (chloroform) | 81.07 (81.19 | 5.66 5.62 | 2.40 2.37) | — |
| 7B | Copper complex of the above Schiff base | 67 | — | +953 (benzene) | 73.38 (73.55 | 5.24 4.78 | 2.38 2.14 | 9.17 9.73) |
| 8A | (S)-N-salicylidene-2-amino-1,1-di(2-benzyloxy-5-methylphenyl)-3-phenyl-1-propanol | 80 | oil | — | — | — | — | — |
| 8B | Copper complex of the above Schiff base | 88 | — | −1830 (benzene) | 74.54 (74.50 | 5.62 5.54 | 2.09 1.98 | 8.22 8.96) |
| 9A | (S)-N-salicylidene-2-amino-1,1-di(5-t-butyl-2-isopropoxyphenyl)-3-phenyl-1-propanol | 80 | oil | — | — | — | — | — |
| 9B | Copper complex of the above Schiff base | 45 | — | −973 (benzene) | 71.98 (72.33 | 7.53 7.37 | 2.10 2.01 | 9.11 9.11) |
| 10A | (R)-N-salicylidene-2-amino-1,1-di(5-t-butyl-2-octyloxyphenyl)-3-phenyl-1-propanol | 80 | oil | — | — | — | — | — |
| 10B | Copper complex of the above Schiff base | 65 | — | +730 (benzene) | 74.71 (74.56 | 8.85 8.54 | 1.73 1.67 | 7.13 7.59) |
| 11A | (R)-N-salicylidene-2-amino-1,1-di(4-butoxybiphenyl-3-yl)-3-phenyl-1-propanol | 77 | 114.8 | +62 (chloroform) | 82.24 (81.90 | 7.43 7.02 | 1.98 1.99) | — |
| 11B | Copper complex of the above Schiff base | 50 | — | +1730 (benzene) | 75.96 (75.32 | 6.59 6.19 | 1.83 1.83 | 8.79 8.30) |
| 12A | (R)-N-salicylidene-2-amino-1,1-di(2,5-dibutoxyphenyl)-3-phenyl-1-propanol | 85 | oil | — | — | — | — | — |
| 12B | Copper complex of the above Schiff base | 50 | — | +1140 (benzene) | 70.41 (69.72 | 7.53 7.31 | 1.67 1.85 | 7.60 8.38) |
| 13A | (S)-N-salicylidene-2-amino-1,1-di(2-isopropoxyphenyl)-3-(4-isopropoxyphenyl)-1-propanol | 85 | oil | — | — | — | — | — |
| 13B | Copper complex of the above Schiff base | 75 | — | −1210 (benzene) | 68.34 (69.08 | 6.53 6.42 | 1.56 2.18 | 9.74 9.88) |
| 14A | (S)-N-salicylidene-2-amino-1,1-di(5-t-butyl-2-octyloxyphenyl)-3-(4-isopropoxyphenyl)-1-propanol | 80 | oil | — | — | — | — | — |
| 14B | Copper complex of the above Schiff base | 70 | — | −720 (benzene) | 74.66 (75.09 | 8.86 8.82 | 1.29 1.59 | 7.22 7.22) |
| 15A | (S)-N-salicylidene-2-amino-1,1-di(2-butoxyphenyl)-3-cyclohexyl-1-propanol | 95 | oil | — | — | — | — | — |
| 15B | Copper complex of the above Schiff base | 93 | — | −814 (benzene) | 68.48 (69.82 | 7.61 7.32 | 2.20 2.26 | 8.99 10.26) |
| 16A | (S)-N-salicylidene-2-amino-1,1-di(2-methoxyphenyl)-4-methyl-1-pentanol | 65 | 142.0 | +165 (chloroform) | 74.62 (74.80 | 7.12 7.21 | 3.04 3.23) | — |
| 16B | Copper complex of the above Schiff base | 70 | — | −1110 (benzene) | 65.59 (65.50 | 6.10 5.91 | 2.71 2.83 | 12.17 12.83) |
| 17A | (S)-N-salicylidene-2-amino-1,1-di(2-butoxy-5-t-butylphenyl)-4-methyl-1-propanol | 80 | oil | — | — | — | — | — |
| 17B | Copper complex of the above Schiff base (S)-N-salicylidene-2-amino- | 87 | — | −540 (benzene) | 70.98 (71.22 | 8.61 8.31 | 2.20 2.03 | 8.70 9.19) |

Table 3-continued

Chiral Schiff bases and binuclear copper complexes

| Example | Compound | Yield (%) | m.p. (°C.) | Specific* rotation (deg.) | C (%) | H (%) | N (%) | Cu (%) |
|---|---|---|---|---|---|---|---|---|
| 18A | 1,1-di(2-benzyloxy-5-t-butyl-phenyl)-4-methyl-1-pentanol | 90 | oil | — | — | — | — | — |
| 18B | Copper complex of the above Schiff base (S)-N-salicylidene-2-amino- | 80 | — | −500 (benzene) | 74.20 (74.33 | 7.04 7.03 | 1.62 1.84 | 8.58 8.37) |
| 19A | 1,1-di(2-butoxy-5-t-butyl-phenyl)-1-propanol | 90 | oil | — | — | — | — | — |
| 19B | Copper complex of the above Schiff base (S)-N-salicylidene-2-amino- | 92 | — | −682 (benzene) | 70.73 (70.56 | 8.37 7.84 | 2.27 2.14 | 8.50 9.70) |
| 20A | 1,1-di(2-butoxyphenyl)-3-methyl-1-butanol | 92 | oil | — | — | — | — | — |
| 20B | Copper complex of the above Schiff base (S)-N-salicylidene-2-amino- | — | — | −929 (benzene) | 66.82 (66.58 | 7.15 7.26 | 2.31 2.59 | 11.3 11.74) |
| 21A | 1,1-di(2-butoxyphenyl)-3-propanol | 93 | 112–113 | +87.8 (chloroform) | 75.58 (75.76 | 7.92 7.84 | 2.91 2.94) | — |
| 21B | Copper complex of the above Schiff base (R)-N-(3,5-dibromosali-cylidene)-2-amino-1,1- | 90 | — | −1077 (benzene) | 71.38 (71.76 | 6.93 7.03 | 2.88 2.79 | 12.40 12.65) |
| 22A | di(2-isopropoxyphenyl)-3-phenyl-1-propanol | 90 | oil | — | — | — | — | — |
| 22B | Copper complex of the above Schiff base (R)-N-(3-ethoxysali-cylidene)-2-amino-1,1- | 86 | — | +840 (ethanol) | 55.41 (54.96 | 4.63 4.48 | 1.99 1.89 | 7.17 8.55) |
| 23A | di(2-isopropoxyphenyl)-3-phenyl-1-propanol | 90 | oil | — | — | — | — | — |
| 23B | Copper complex of the above Schiff base (R)-N-(2-hydroxy-1-naphthylmethylene)-2- | 90 | — | +1140 (ethanol) | 68.27 (68.72 | 6.26 6.25 | 2.22 2.23 | 9.88 10.10) |
| 24A | amino-1,1-di(2-isopro-poxyphenyl)-3-phenyl-1-propanol | 90 | oil | — | — | — | — | — |
| 24B | Copper complex of the above Schiff base N-salicylidene(S)-2- | 49 | — | +1180 (ethanol) | 71.98 (71.85 | 6.04 5.87 | 2.29 2.20 | 8.78 10.00) |
| 25A | amino-1,1-di(2-3'-oxa-pentoxy-5-t-butyl-phenyl)-1-propanol | 80 | oil | — | — | — | — | — |
| 25B | Copper complex of the above Schiff base N-salicylidene(S)-2- | 85 | — | −300 | 67.33 (66.99 | 7.12 7.54 | 2.31 2.06 | 9.50 9.33) |
| 26A | amino-1,1-di(2-cyclo-hexyloxy-5-t-butyl-phenyl)-1-propanol | 90 | 78.6 | +155 | 79.10 (78.87 | 8.90 8.92 | 2.00 2.19) | — |
| 26B | Copper complex of the above Schiff base N-salicylidene(R)-2-amino-1,1-di(2-cyclo- | 90 | 160° (dec.) | −848 | 72.10 (71.95 | 8.12 7.85 | 2.13 2.00 | 10.00 9.07) |
| 27A | hexyloxy-5-t-butyl-phenyl)-3-phenyl-1-propanol | 85 | oil | — | — | — | — | — |
| 27B | Copper complex of the above Schiff base N-salicylidene(S)-2- | 80 | 150° | +697 | 75.21 (74.18 | 7.51 7.60 | 2.23 1.80 | 9.37 8.18) |
| 28A | amino-1,1-di(2-t-butoxy-5-t-butylphenyl)-1-propanol | 85 | oil | — | — | — | — | — |
| 28B | Copper complex of the above Schiff base N-salicylidene(S)-2- | 72 | — | −510 | 69.21 (70.56 | 7.94 7.84 | 2.29 2.14 | 9.14 9.70) |
| 29A | amino-1,1-di(2-iso-propoxy-5-methylphenyl)-1-propanol | 90 | oil | — | — | — | — | — |
| 29B | Copper complex of the above Schiff base N-salicylidene(S)-2- | 88 | — | −1090 | 67.16 (67.08 | 6.83 6.57 | 2.62 2.61 | 12.89 11.83) |
| 30A | amino-1,1-di(2-benzyl-oxy-4-t-butylphenyl)-1-propanol | 80 | oil | — | — | — | — | — |
| 30B | Copper complex of the above Schiff base N-salicylidene(S)-2- | 39 | — | −590 | 75.74 (73.67 | 6.63 6.60 | 2.15 1.95 | 7.68 8.86) |
| 31A | amino-1,1-di(2-sec-butoxy-5-t-butylphenyl)-1-propanol | 80 | oil | — | — | — | — | — |
| 31B | Copper complex of the above Schiff base N-salicylidene(S)-2- | 75 | — | −1000 | 69.56 (70.29 | 8.29 7.92 | 2.42 2.16 | 9.53 9.79) |
| 32A | amino-1,1-di(2-benzyloxy-5-t-butyl-phenyl)-1-propanol | 85 | oil | — | — | — | — | — |
| 32B | Copper complex of the | 32 | — | −533 | 74.15 | 6.90 | 1.94 | 8.30 |

Table 3-continued

Chiral Schiff bases and binuclear copper complexes

| Example | Compound | Yield (%) | m.p. (° C.) | Specific* rotation (deg.) | C (%) | H (%) | N (%) | Cu (%) |
|---|---|---|---|---|---|---|---|---|
| | above Schiff base | | | | (73.67 | 6.60 | 1.95 | 8.86) |
| 33A | N-salicylidene(S)-2-amino-1,1-di(2-butoxy-4-t-butylphenyl)-1-propanol | 85 | oil | — | — | — | — | — |
| 33B | Copper complex of the above Schiff base | 87 | — | −274 | 70.55 (70.29 | 8.10 7.92 | 2.03 2.16 | 10.21 9.79) |
| 34A | N-salicylidene(S)-2-amino-1,1-di(2,5-dibutoxyphenyl)-1-propanol | 92 | 69–71 | +969 | — | — | — | — |
| 34B | Copper complex of the above Schiff Base | 73 | — | −1380 | 67.37 (68.49 | 7.96 7.87 | 2.44 2.10 | 10.1 9.54) |
| 35A | N-salicylidene(S)-2-amino-1,1-di(4-octyloxy-3-biphenyl)-1-propanol | 76 | 128–129 | +70.1 | 79.77 (81.15 | 8.64 8.31 | 1.64 1.89) | — |
| 35B | Copper complex of the above Schiff base | 98 | — | −1498 | 75.54 (74.92 | 7.80 7.42 | 1.67 1.75 | 9.50 7.93) |
| 36A | N-salicylidene(S)-2-amino-1,1-di(4-butoxy-3-biphenyl)-1-propanol | 93 | 169.5–170.5 | +73.3 | 79.87 (80.35 | 7.53 7.22 | 2.15 2.23) | — |
| 36B | Copper complex of the above Schiff base | 93 | — | — | 70.79 (73.18 | 6.56 6.29 | 1.60 2.03 | 8.90 9.22) |
| 37A | N-salicylidene(S)-2-amino-1,1-di(5-t-butyl-2-octyloxyphenyl)-1-propanol | 98 | oil | −25.5 | — | — | — | — |
| 37B | Copper complex of the above Schiff base | 86 | — | −550 | 72.12 (72.55 | 8.90 8.87 | 2.13 1.84 | 8.50 8.34) |
| 38A | N-salicylidene(S)-2-amino-1,1-di(2-butoxy-5-methylphenyl)-1-propanol | 79 | 119–125 | +91.3 | 76.74 (76.31 | 8.32 8.20 | 2.74 2.78) | — |
| 38B | Copper complex of the above Schiff base | 97 | — | −1352 | 65.25 (68.00 | 7.66 6.96 | 2.40 2.48 | 10.2 11.24) |
| 39A | N-salicylidene(S)-2-amino-1,1-di(2-butoxy-5-t-butylphenyl)-3-(4-benzyloxyphenyl)-1-propanol | 90 | oil | — | — | — | — | — |
| 39B | Copper complex of the above Schiff base | 80 | — | −690 | 74.47 (73.66 | 7.83 7.39 | 1.46 1.68 | 6.37 7.64) |
| 40A | N-salicylidene(S)-2-amino-1,1-di(2-butoxy-5-t-butylphenyl)-3-methyl-1-butanol | 80 | oil | — | — | — | — | — |
| 40B | Copper complex of the above Schiff base | 88 | — | −789 | 70.37 (70.92 | 8.70 8.18 | 2.04 2.07 | 9.54 9.38) |
| 41A | N-salicylidene(S)-2-amino-1,1-di(2-butoxyphenyl)-4-methyl-1-pentanol | 88 | oil | — | — | — | — | — |
| 41B | Copper complex of the above Schiff base | 99 | — | −647 | 69.51 (68.43 | 7.94 7.12 | 2.64 2.42 | 9.40 10.97) |

*Specific rotations are shown as $[\alpha]_D$ (chloroform) for Schiff bases and as $[\alpha]_{546}$ (benzene) for copper complexes unless otherwise specified.
**Calculated values are shown in parenthesis.

EXAMPLE 42C

To a suspension of 0.43 g. (1.4 millimols) of bis(salicylaldehydate) copper in 10 ml. methanol was added dropwise a solution of 1.1 g. (3.0 millimols) of (R)-2-amino-1,1-di(2-methoxyphenyl)-3-phenyl-1-propanol {$[\alpha]_D$ +42.3° (c 1.1, chloroform)} in 10 ml. of methanol. The addition was carried out under thorough stirring at room temperature. The period of the addition was one hour and the reaction mixture was stirred for another one hour. The resulting solids were collected by filtration, washed with methanol and dried under reduced pressure to give a mononuclear complex of (R)-N-salicylidene-2-amino-1,1-di(2-methoxyphenyl)-3-phenyl-1-propanol as grayish blue crystals.

Yield, 0.75 g. (58%), $[\alpha]_{546}$, +860° (c 0.065, benzene), melting point: 205° – 206° C. (decomposed).

| Elemental analysis for $C_{60}H_{54}CuN_2O_8$ | | | | |
|---|---|---|---|---|
| | C (%) | H (%) | N (%) | Cu (%) |
| Found: | 71.87 | 5.57 | 3.00 | 5.82 |
| Calculated: | 72.31 | 5.66 | 2.81 | 6.38 |

Magnetic susceptibility $\mu$ = 1.78 B.M.

EXAMPLES 43C and 44C

In a similar manner to Example 42C, other two kinds of chiral mononuclear copper complexes of the formula (III) were synthesized from chiral amino alcohols of the formula (IV) and bis (salicylaldehydato) copper. The results are summarized in Table 4.

Table 4

| | | | | Specific* | Elemental analysis** | | | |
|---|---|---|---|---|---|---|---|---|
| | | | | | C | H | N | Cu |
| Example | Compound | Yield (%) | m.p. (°C.) | rotation (deg) | (%) | (%) | (%) | (%) |
| 43C | Mononuclear copper complex of (R)-N-salicylidene-2-amino-1,1-di(3-methoxyphenyl)-3-phenyl-1-propanol | 50 | — | — | 71.22 (72.31 | 5.23 5.66 | 2.60 2.81 | 6.52 6.38) |
| 44C | Mononuclear copper complex of (S)-N-salicylidene-2-amino-1,1-di(2-methoxyphenyl)-4-methyl-1-pentanol | 60 | — | −620 (benzene) | 69.12 (69.84 | 6.37 6.51 | 2.92 3.02 | 7.42 6.84) |

* Specific rotations are shown as $[\alpha]_D$ for Schiff based and as $[\alpha]_{564}$ for copper complexes. Solvents are shown in parentheses.
** Calculated values are shown in parentheses.

What we claim is:

1. A compound which is a copper complex coordinated with a chiral Schiff base of the formula:

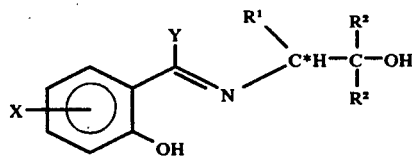

wherein C is an asymmetric carbon atom, $R^1$ is selected from the group consisting of (a) alkyl groups whose carbon atom number is 1–10, and (b) aralkyl groups with or without alkoxy substituent(s), whose total carbon atom number is 7–20, $R^2$ is selected from aryl groups with alkoxy substituent(s), whose total carbon atom number is 7–30, X is selected from the group consisting of (a) hydrogen, (b) alkyl groups having 1–10 carbon atoms, (c) phenyl group, (d) alkoxy groups having 1–10 carbon atoms, (e) halogen atoms, (f) nitro, or X is benzo which together with the ring to which it is attached forms a naphthalene ring, and Y is a hydrogen atom.

2. A compound of claim 1 in which said copper complex has the following structure:

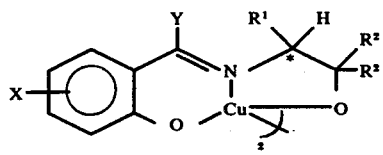

wherein $R^1$ $R^2$, X and Y are defined as in claim 1.

3. The compound of claim 1 in which said copper complex has the following structure:

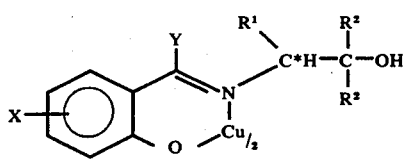

wherein C, $R^1$, $R^2$, X and Y are defined as in claim 1.

4. The compound of claim 1 in which $R^1$ is
a. benzyl,
b. 4-methoxyphenylmethyl,
c. 4-isopropoxyphenylmethyl,
d. 4-butoxyphenylmethyl,
e. 4-benzyloxyphenylmethyl,
f. methyl,
g. isopropyl,
h. isobutyl, or
i. cyclohexylmethyl.

5. The compound of claim 1 in which $R^2$ is
a. 2-methoxyphenyl,
b. 2-ethoxyphenyl,
c. 2-isopropoxyphenyl,
d. 2-butoxyphenyl,
e. 2-octyloxyphenyl,
f. 2-benzyloxy-5-methylphenyl, p1 g. 2-butoxy-5-t-butylphenyl,
h. 5-t-butyl-2-octyloxyphenyl,
i. 4-butoxybiphenyl-3-yl, or
j. 2,5-dibutoxyphenyl.

6. The compound of claim 2 in which said chiral Schiff base is either an (R)- or (S)-enantiomer of the following:
a. N-salicylidene-2-amino-1,1-di(2-isopropoxyphenyl)-3-phenyl-1-propanol,
b. N-salicylidene-2-amino-1,1-di(2-butoxy-5-t-butylphenyl)-3-phenyl-1-propanol,
c. N-salicylidene-2-amino-1,1-di(2-methoxyphenyl)-3-phenyl-1-propanol,
d. N-salicylidene-2-amino-1,1-di(2-ethoxyphenyl)-3-phenyl-1-propanol,
e. N-salicylidene-2-amino-1,1-di(2-butoxyphenyl)-3-phenyl-1-propanol,
f. N-salicylidene-2-amino-1,1-di(2-octyloxy-phenyl)-3-phenyl-1-propanol,
g. N-salicylidene-2-amino-1,1-di(2-phenoxyphenyl)-3-phenyl-1-propanol,
h. N-salicylidene-2-amino-1,1-di(2-benzyloxy-5-methylphenyl)-3-phenyl-1-propanol,
i. N-salicylidene-2-amino-1,1-di(5-t-butyl-2-isopropoxyphenyl)-3-phenyl-1-propanol,
j. N-salicylidene-2-amino-1,1-di(5-t-butyl-2-octyloxyphenyl)-3-phenyl-1-propanol,
k. N-salicylidene-2-amino-1,1-di(4-butoxybiphenyl-3-yl)-3-phenyl-1-propanol,
l. N-salicylidene-2-amino-1,1-di(2,5-dibutoxyphenyl)-3-phenyl-1-propanol,
m. N-salicylidene-2-amino-1,1-di(2-isopropoxyphenyl)-3-(4-isopropoxyphenyl)-1-propanol,
n. N-salicylidene-2-amino-1,1-di(5-t-butyl-2-octyloxyphenyl)-3-(4-isopropoxyphenyl)-1-propanol,
o. N-salicylidene-2-amino-1,1-di(2-butoxyphenyl)-3-cyclohexyl-1-propanol,
p. N-salicylidene-2-amino-1,1-di(2-methoxyphenyl)-4-methyl-1-pentanol,
q. N-salicylidene-2-amino-1,1-di(2-butoxy-5-t-butylphenyl)-4-methyl-1-pentanol, r. N-salicylidene-2-amino-1,1-di(2-benzyloxy-5-t-butylphenyl)-4-methyl-1-pentanol,
s. N-salicylidene-2-amino-1,1-di(2-butoxy-5-t-butylphenyl)-1-propanol,
t. N-salicylidene-2-amino-1,1-di(2-butoxyphenyl)-3-methyl-1-butanol,
u. N-salicylidene-2-amino-1,1-di(2-butoxyphenyl)-1-propanol,
v. N-(3,5-dibromosalicylidene)-2-amino-1,1-di(2-isopropoxyphenyl)-3-phenyl-1-propanol,
w. N-(3-ethoxysalicylidene)-2-amino-1,1-di(2-isopropoxyphenyl)-3-phenyl-1-propanol,
x. N-(2-hydroxy-1-naphthylmethylene)-2-amino-1,1-di(2-isopropoxyphenyl)-3-phenyl-1-propanol, or
y. N-salicylidene-2-amino-1,1-di(4-butoxybiphenyl-3-yl)-1-propanol.

7. The compound of claim 3 in which said chiral Schiff base is either an (R)- or (S)-enantiomer of the following:
a. N-salicylidene-2-amino-1,1-di(2-methoxyphenyl)-3-phenyl-1-propanol,
b. N-salicylidene-2-amino-1,1-di(3-methoxyphenyl)-3-phenyl-1-propanol, or
c. N-salicylidene-2-amino-1,1-di(2-methoxyphenyl)-4-methyl-1-pentanol.

* * * * *